United States Patent
Hampton

(10) Patent No.: US 8,222,300 B2
(45) Date of Patent: Jul. 17, 2012

(54) METHODS OF TREATING PARKINSON'S DISEASE USING HALOGENATED VOLATILE COMPOUNDS

(75) Inventor: Thomas G. Hampton, Framingham, MA (US)

(73) Assignee: Mouse Specifics, Inc., Quincy, MA (US)

( * ) Notice: Subject to any disclaimer, the term of this patent is extended or adjusted under 35 U.S.C. 154(b) by 269 days.

(21) Appl. No.: 12/530,822

(22) PCT Filed: Mar. 17, 2008

(86) PCT No.: PCT/US2008/003500
§ 371 (c)(1),
(2), (4) Date: Sep. 11, 2009

(87) PCT Pub. No.: WO2008/112319
PCT Pub. Date: Sep. 18, 2008

(65) Prior Publication Data
US 2010/0047187 A1    Feb. 25, 2010

Related U.S. Application Data

(60) Provisional application No. 60/981,147, filed on Mar. 15, 2007.

(51) Int. Cl.
*A01N 29/00* (2006.01)
*A61K 31/02* (2006.01)
(52) U.S. Cl. ........................................ 514/743; 514/816
(58) Field of Classification Search .................. None
See application file for complete search history.

(56) References Cited

U.S. PATENT DOCUMENTS

2003/0233086 A1 * 12/2003 Burns et al. ................... 604/512

OTHER PUBLICATIONS

Wood-Kaczmar et al. "Understanding the molecular causes of Parkinson's disease" TRENDS in Molecular Medicine 2006, vol. 12, No. 11, pp. 521-528.*
Pahapill et al., "The pedunculopontine nucleus and Parkinson's disease" Brain, 2000, vol. 123, pp. 1767-1783.*
Caraiscos et al., "Selective enhancement of tonic GABAergic inhibition in murine hippocampal neurons by low concentrations of the volatile anesthetic isoflurane" The Journal of Neuroscience, 2004, vol. 24, No. 39, pp. 8454-8458.*
Burton et al., "Anesthesia in elderly patients with neurodegerative disorder: special considerations," Drugs & Aging. 21(4):229-242 (2004).
Eckenhoff et al., "Anesthetics and Neurodegenerative Disorders; a molecular basis for concern?" Anesthesiology Abstracts of Scientific Papers Annual Meeting. 2003:A848 (2003).
Eckenhoff et al., "Inhaled anesthetic enhancement of amyloid-[beta] oligomerization and cytotoxicity," Anesthesiology. 101(3):703-709 (2004).
Muravchick et al., "Parkinsonian symptoms during emergence from general anesthesia," Anesthesiology. 82(1):305-307 (1995).

* cited by examiner

*Primary Examiner* — James H. Alstrum-Acevedo
*Assistant Examiner* — Daniel L Branson
(74) *Attorney, Agent, or Firm* — Sean D. Detweiler, Esq.; Morse, Barnes-Brown & Pendleton, P.C.

(57) ABSTRACT

The present invention provides methods of using halogenated volatile compounds, e.g., halogenated ether, for treating a neurological disorder, e.g., Parkinson's disease.

17 Claims, No Drawings

METHODS OF TREATING PARKINSON'S DISEASE USING HALOGENATED VOLATILE COMPOUNDS

RELATED APPLICATIONS

This application is a national stage filing under 35 U.S.C. 371 of International Application PCT/US2008/003500, filed Mar. 17, 2008, which claims the benefit of U.S. Ser. No. 60/981,147, entitled "Methods of Treating Parkinson's Disease Using Halogenated Volatile Compounds," filed on Mar. 15, 2007. The entire contents of these applications are hereby incorporated herein by reference. International Application PCT/US2008/003500 was published under PCT Article 21(2) in English.

BACKGROUND OF THE INVENTION

Parkinson's disease (also known as Parkinson disease or PD) is a degenerative disorder of the central nervous system that often impairs motor skills and speech. Parkinson's disease belongs to a group of conditions called movement disorders. It is characterized by muscle rigidity, tremor, a slowing of physical movement (bradykinesia), and in extreme cases, a loss of physical movement (akinesia).

The cause of Parkinson's disease is largely unknown; however, the disease is associated with a substantial loss of dopaminergic neurons in the pars compacta region of the substantia nigra.

The main therapy currently being used for treating Parkinson's disease is L-DOPA treatment. However, L-DOPA has many undesirable side-effects associated with it including, for example, nausea, vomiting, postural hypotension, confusion or, when the treatment is continued for extended periods of time, dyskinesia. Other available therapies including dopamine agonists, anticholinergic drugs, catechol-0-methyl-transferase inhibitors or amantadine, are less effective and also associated with a number of often serious side-effects.

Accordingly, there is a need for a therapy, which could help Parkinson's disease sufferers and reduce the number or severity of side-effects in comparison with the available treatment methods.

SUMMARY OF THE INVENTION

The present invention is based, at least in part, on the surprising and unexpected discovery that halogenated volatile compounds, e.g., isoflurane, which are typically used as anesthetics, can be used for treating or preventing Parkinson's disease (PD), and for improving gait in Parkinson's patients. Accordingly, the present invention provides methods of administering a halogenated volatile compound, e.g., isoflurane, to a subject having, at a risk of developing, or genetically, metabolically, or environmentally predisposed to develop symptoms of Parkinson's disease, in order to improve gait and/or to treat, prevent and/or ameliorate the onset, advancement, severity or effects of Parkinson's disease in the subject, e.g., by increasing dopamine turnover or e.g. modulation of gamma-aminobutyric acid (GABA) or GABA receptors.

In one embodiment, the present invention provides a method of treating or preventing Parkinson's disease in a subject in need thereof comprising administering a therapeutically effective amount of a halogenated volatile compound to the subject, such that the Parkinson's disease is treated or prevented.

In one embodiment the halogenated volatile compound is selected from the group consisting of a halogenated ether, a halogenated alkane, and a halogenated benzene. In another embodiment, the halogenated volatile compound is a halogenated ether, e.g., isoflurane.

In another embodiment, the present invention provides a method of improving gait in a subject having Parkinson's disease comprising administering a therapeutically effective amount of a halogenated volatile compound to the subject and measuring stride length in the subject, wherein an increase in stride length in the subject following administration of the halogenated volatile compound relative to the stride length in the absence of the halogenated volatile compound is indicative of an improvement in gait in the subject having Parkinson's disease.

In yet another embodiment, the present invention provides a method of treating or preventing Parkinson's disease in a subject comprising: (a) administering a pharmaceutically effective amount of a halogenated volatile compound to the subject; and b) measuring stride length in the subject, where an increase in the stride length in the presence of the compound relative to the stride length in the absence of the compound is indicative of treatment or prevention of Parkinson's disease.

In one embodiment, the stride length in a subject is measured as the subject ambulates on a treadmill.

In various embodiments, the halogenated volatile compound is in gaseous form. Exemplary halogenated volatile compounds include, but are not limited to, e.g., isoflurane, desflurane, enflurane, halothane, and sevoflurane. In one embodiment, the halogenated volatile compound is administered in combination with oxygen and/or carbon dioxide. In one embodiment, the halogenated volatile compound is administered to the subject in combination with an additional therapeutic agent.

In one embodiment, the halogenated volatile compound, e.g., isoflurane is administered using an inhaler.

In one embodiment, the halogenated volatile compound, e.g., isoflurane, is administered in a chamber whereby the subject is exposed to the chamber. The subject may be entirely or partially in the chamber.

In one embodiment, the subject further comprises reduced stride frequency and reduced stance width variability or stride length variability in the presence of a halogenated volatile compound, e.g., isoflurane, relative to the stride frequency and stance width variability or stride length variability in the absence of the compound.

Other features and advantages of the invention will be apparent from the following detailed description, and from the claims.

DETAILED DESCRIPTION OF THE INVENTION

In order that the present invention may be more readily understood, certain terms are first defined. Additional definitions are set forth throughout the detailed description.

The term "halogenated volatile compound," as used herein, refers to any compound which depresses central nervous system function. Halogenated volatile compounds are well known in the art for their anesthetic properties and exemplary halogenated volatile compounds include, but are not limited to, a halogenated ether, a halogenated alkane, and a halogenated benzene. In one embodiment, the halogenated volatile compound is a halogenated ether, e.g., isoflurane. Other examples of halogenated volatile compounds include, but are not limited to, isoflurane (2-chloro-2-(difluoromethoxy)-1,1,1-trifluoro-ethane), desflurane (2-(difluoromethoxy)-1,1,1, 2-tetrafluoro-ethane), enflurane (2-chloro-1,1,2-trifluoroethyl difluoromethyl ether), halothane (2-bromo-2-chloro-1,1,1-trifluoro-ethane), and sevoflurane (2,2,2-trifluoro-1-[trifluoromethyl]ethyl fluoromethyl ether or fluoromethyl hexafluoroisopropyl ether).

As used herein, the term "gait" refers to a sequence of paw/foot or limb movements by which a subject (e.g., a human, mouse or other animal) moves, or attempts to move, in a directional manner. In exemplary usage, the direction of movement is forward. Also in exemplary usage, the term "gait" refers to a rhythmic and/or cyclical ambulatory process performed by at least one limb of a subject; however, the rhythm and/or cyclicality of a subject's ambulatory process can be highly disrupted, with the process still properly characterized as "gait." A subject having Parkinson's disease may exhibit a certain gait, often referred to as "Parkinson's gait," which is characterized by a number of features, including shuffling, a decreased stride length, and/or gait speed. Other features commonly associated with Parkinson's gait are shuffling, head down, shoulders drooped, lack of arm swing, and leaning backwards or forwards unnaturally. In subjects having Parkinson's disease, initiating walking is difficult and freezing mid-stride may occur. Gait can be measured using any art recognized technique and as described in, for example, U.S. Pat. No. 6,899,686, the entire contents of which are incorporated by reference herein.

It is understood that any suitable means for the measurement of gait may be used in the methods of the invention. For example, in one embodiment, the apparatus can take the form of a gait imaging system, which includes a moveable belt track upon which a subject can ambulate. In one embodiment, the imaging system includes one or more imaging devices for recording the gait of an ambulating subject on the belt track. In another embodiment, an imaging device is disposed below the belt track to record contact between at least one forelimb of the subject and the belt track. However, it is understood that one or more imaging devices could be disposed anywhere with respect to the belt track, as long as such devices are able to record the gait of a subject ambulating on the belt track. The subject can ambulate along the belt track in a substantially stationary location above the imaging device as the belt track moves, and the imaging device can record the contact by the subject. An exemplary gait measuring system that can be used is disclosed in U.S. Pat. No. 6,899,686, incorporated by reference in its entirety herein.

Improvements in the gait of a subject having Parkinson's may also be measured according to standard methods known in the art, including, but not limited to, hip flexion contracture, hamstring muscle length, 6- and 10-meter walk distance, turning while standing, the Timed Get Up and Go (TUG) test (a gross measure of balance and lower extremity function) (see Mathias et al. (1986) *Arch Phys Med Rehabil* 67:387; Morris et al. (2001) *Phys Ther* 81:810; Okumiya (1998) *J Am Geriatr Soc* 46:928; and Shumway-Cook (2000) *Phy Ther* 80:896), the Berg Balance Scale, the Unified Parkinson's Disease Rating Scale (UPDRS) (see Fahn, S.; Elton, R.; Members of the UPDRS development committee. Unified Parkinson's disease rating scale. In: Fahn et al., editor. Recent developments in Parkinson's disease. NJ, Florham Park:; 1987. pp. 153-163) the Functional Reach test (see also Schenkman et al. (1997) *Phy Ther* 77:19 and Lim et al. (2005) *Parkinsonism and Related Disorders* 11:19). Other examples of means by which the gait of a subject may be determined are described in US Patent Publication 20070250134. An example of how to determine improvements in the gait, stride, and/or swing of a subject having Parkinson's disease is also described in Frenkel-Toledo et al. (2005) *J Neuroengineering Rehabil* 2:23, incorporated by reference herein in its entirety. Each of the foregoing references is incorporated by reference herein.

As used herein, the term "improving gait" or "improvement in gait" refers to one or more of an increase in stride length, a decrease or reduction in stride frequency and/or a decrease or reduction in stance width variability and/or a decrease in stride length variability in a subject following administration of a halogenated volatile compound, e.g., a halogenated ether, to the subject, relative to the stride length, stride frequency, stance width variability, and/or stride length variability in the absence of the compound.

As used herein, the term "stride length" refers to the distance traveled during one cycle of gait (e.g., the distance traveled between the point at which a foot, paw, knee, hand, etc. of a moving (e.g., ambulating) subject departs contact with a primary supporting surface (e.g., the ground or other walking surface) and the point at which the same foot, paw, knee, hand, etc. of the subject next contacts the supporting surface. As used herein, the term "standardized average stride length" refers to the average measured value for stride length observed for a population that has not been selected for, or is not anticipated to have been selected for, a disease, disorder or any other attribute that alters, or would be anticipated to alter, the measured average stride length of the population. In one embodiment, the present invention provides a method of increasing stride length in a subject having Parkinson's disease or susceptible to developing Parkinson's disease by administering a halogenated volatile compound to a subject. The increase in stride length following administration of the halogenated volatile compound can be any increase, e.g., at least 5%, 10%, 20%, 30%, 40%, 50%, 60%, 70%, 80%, 90% 95%, 96%, 97%, 98%, 99% or more, relative to the stride length in the absence of the compound. In a particular embodiment, the stride length following administration of the halogenated volatile compound is greater than the standardized average stride length.

The term "stride frequency," as used herein, refers the number of strides taken in a given amount of time or over a given distance. In one embodiment, the present invention provides a method of decreasing stride frequency in a subject having Parkinson's disease or susceptible of developing Parkinson's disease, by administering a halogenated volatile compound to the subject. The decrease in stride frequency following administration of the halogenated volatile compound can be any decrease, e.g., at least 5%, 10%, 20%, 30%, 40%, 50%, 60%, 70%, 80%, 90% 95%, 96%, 97%, 98%, 99% or more, relative to the stride frequency in the absence of the compound.

In another embodiment, the present invention provides a method of decreasing stance width variability in a subject having Parkinson's disease or susceptible of developing Parkinson's disease, by administering a halogenated volatile compound to the subject. The decrease in stance width variability following administration of the halogenated volatile compound can be any decrease, e.g., at least 5%, 10%, 20%, 30%, 40%, 50%, 60%, 70%, 80%, 90% 95%, 96%, 97%, 98%, 99% or more, relative to the stance width variability in the absence of the compound.

In another embodiment, the present invention provides a method of decreasing stride length variability in a subject having Parkinson's disease or susceptible of developing Parkinson's disease, by administering a halogenated volatile compound to the subject. The decrease in stride length variability following administration of the halogenated volatile compound can be any decrease, e.g., at least 5%, 10%, 20%, 30%, 40%, 50%, 60%, 70%, 80%, 90% 95%, 96%, 97%, 98%, 99% or more, relative to the stride length variability in the absence of the compound.

As used herein, the term "subject" includes any human or non-human animal. For example, the methods of the present invention can be used to treat a subject having Parkinson's disease. In a particular embodiment, the subject is a human.

The terms "treat," "treating," and "treatment," as used herein, refer to therapeutic or preventative measures described herein. The methods of "treatment" employ administration to a subject, a halogenated volatile compound, for example, a subject having Parkinson's disease or predisposed to having Parkinson's disease, in order to prevent, cure, delay, reduce the severity of, or ameliorate one or more symptoms of Parkinson's disease or recurring Parkinson's disease, or in order to prolong the survival of a subject beyond that expected in the absence of such treatment.

In one embodiment, administration of a halogenated volatile compound, e.g., isoflurane to a subject having or at risk of developing Parkinson's disease can improve gait, e.g., increase stride length, reduce stride frequency and/or reduce stance width variability, and also prevent, treat, delay, mitigate and/or ameliorate the onset, advancement, severity and/or symptoms of Parkinson's disease by, e.g., increasing dopamine turnover.

The term, "therapeutically effective amount," as used herein, refers to an amount or dose of a halogenated volatile compound including, but not limited to, for example, isoflurane, desflurane, enflurane, halothane, and sevoflurane, which results in an increase in stride length, or a reduction in stride frequency and/or stance width variability and/or reduction in stride length variability in a subject. A therapeutically effective amount will vary depending upon the subject and the weight and age of the subject, the severity of the disease condition, the manner of administration and the like, which can readily be determined by one of ordinary skill in the art.

One aspect of the invention is a composition comprising a halogenated volatile compound, including, but not limited to, isoflurane and oxygen and/or carbon dioxide. In one embodiment, the halogenated volatile compound is combined with oxygen. In another embodiment, the halogenated volatile compound is combined with a certain percentage of oxygen, e.g., 100%, 99%, 98%, 97%, 96%, 95%, 94%, 93%, 92%, 91%, 90%, 89%, 88%, 87%, 86%, 85%, 84%, 83%, 82%, 81%, 80%, and so forth. In another embodiment, the halogenated volatile compound is combined with a certain percentage of oxygen and a certain percentage of $CO_2$ (carbon dioxide). For example, the halogenated volatile compound may be combined with 99% oxygen/1% $CO_2$, 98% oxygen/2% $CO_2$, 97% oxygen/3% $CO_2$, 96% oxygen/4% $CO_2$, 95% oxygen/5% $CO_2$, and so forth to 7% oxygen/93% $CO_2$, 6% oxygen/94% $CO_2$, and 5% oxygen/95% $CO_2$. In one embodiment, isoflurane is combined with an oxygen/carbon dioxide ratio ranging from 95% oxygen/5% carbon dioxide to 5% oxygen/95% carbon dioxide. The isoflurane may, for example, be a liquid that is vaporized into oxygen or the combination of oxygen and carbon dioxide. In one embodiment, isoflurane is combined with oxygen or the combination of oxygen and carbon dioxide at a final concentration of 2% to 5% isoflurane. In embodiment, isoflurane is combined with oxygen or the combination of oxygen and carbon dioxide at a final concentration of 2.5% isoflurane.

The halogenated volatile compounds can be incorporated into pharmaceutical compositions suitable for administration. For example, the halogenated volatile compounds can be given alone or as a pharmaceutical composition containing, for example, 0.001, 0.005, 0.01, 0.1, 1, 10, 20, 30, 40, 50, 60, 70, 80, 90, 95, 96, 97, 98, 99 or 100% of active ingredient, e.g., halogenated volatile compound, in combination with a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is typically formulated to be compatible with its intended route of administration. Examples of routes of administration include parenteral, e.g., intravenous, intradermal, subcutaneous, intraperitoneal, intramuscular, oral, inhalation, transdermal (topical), and transmucosal administration.

In a particular embodiment, a pharmaceutical composition is administered by inhalation. For administration by inhalation, the compounds are delivered in the form of an aerosol spray from pressured container or dispenser which contains a suitable propellant, e.g., a gas such as carbon dioxide, or a nebulizer.

Alternatively, the halogenated volatile compound, e.g., isoflurane, may be administered to the subject using a chamber, whereby the subject is exposed to the compound through the chamber. The subject may be entirely or partially within the limits of the chamber for delivery of the halogenated volatile compound, e.g., isoflurane.

The amount of time needed to deliver the halogenated volatile compound to the subject for improving symptoms in the subject relating to Parkinson's disease may vary according to the desired effect, the concentration of anesthetic, and, in one embodiment, the relative combination of $O_2$ and $CO_2$. In one embodiment, the subject inhales the halogenated volatile compound for at least 1 second. In another embodiment the subject inhales the halogenated volatile compound for at least 10 seconds, at least 15 seconds, at least 20 seconds, at least 25 seconds, at least 30 seconds, at least 35 seconds, at least 40 seconds, at least 45 seconds, at least 50 seconds, at least 55 seconds, at least one minute, at least one minute and 15 seconds, at least one and a half minutes, and so forth. In another embodiment, the subject is administered the halogenated volatile compound for a time period ranging from 1 second to 5 minutes.

In one embodiment, an amount of a halogenated volatile compound administered to a subject in order to achieve a desired result, can either be an amount determined using well known standards, for example, Minimum Alveolar Concentration (MAC), which is generally defined as the concentration in the alveolar that prevents a response to a painful stimulus in 50% of subjects.

Actual dosage levels of the active ingredients, e.g., halogenated volatile compound, in the pharmaceutical compositions of the present invention may be varied so as to obtain an amount of the active ingredient which is effective to achieve the desired therapeutic response for a particular patient, composition, and mode of administration, without being toxic to the patient. A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. In general, a suitable daily dose of a composition of the invention will be that amount of the compound which is the lowest dose effective to produce a therapeutic effect. If desired, the effective daily dose of a therapeutic composition may be administered as two, three, four, five, six or more sub-doses administered separately at appropriate intervals throughout the day, optionally, in unit dosage forms.

Also included in the invention are methods and compositions comprising combination of a halogenated volatile compound, e.g., isoflurane, and an additional therapeutic agent, wherein the combination therapy is used to improve the gait of a subject having Parkinson's disease. Examples of additional therapeutic agents which may be combined with a halogenated volatile compound, include, but are not limited to, Deprenyl amantadine or anticholinergic medications, Levedopa, Carbidopa, Entacapone, Pramipexole, ropinirole, Rasagiline, and neupro.

Also encompassed by the present invention is a kit for treating, preventing or managing Parkinson's disease including one or more doses of a therapeutic composition including a halogenated volatile compound and instructions and/or promotional materials for using the composition. The invention further includes kits which describe the combined use of a halogenated volatile compound, e.g., isoflurane, and an additional therapeutic agent for the treatment of Parkinson's disease, including, but not limited to, Deprenyl amantadine or anticholinergic medications, Levedopa, Carbidopa, Entacapone, Pramipexole, ropinirole, Rasagiline, and neupro. In one embodiment, the kit includes a label or package insert which indicates that the agent may be used in combination with a halogenated volatile compound, e.g., isoflurane, for the treatment of Parkinson's disease, including, but not limited to, improvement in the gait of a subject having Parkinson's disease.

The following example provides an illustrative embodiment of the present invention. One of ordinary skill in the art will recognize the numerous modifications and variations that may be performed without altering the spirit and scope of the present invention. Such modifications and variations are encompassed within the scope of the invention. The example does not in any way limit the present invention.

EXAMPLE

Example 1

Isoflurane Improves Gait in Mice

Isoflurane is a halogenated inhalation anesthetic and is routinely used in laboratory animals for its anesthetic properties. In this experiment, posture and gait in mice after brief isoflurane anesthesia was investigated.

Ventral plane videography was used to image 4 adult female CD-1 mice walking 25 cm/s on a transparent treadmill belt just prior to 5 minutes of isoflurane (2.5% isoflurane final concentration in 100% oxygen) anesthesia. Gait analysis was again performed at 25 cm/s 1, 15, 30 and 60 minutes after the animals regained their righting reflex. Mice were placed in a chamber and delivered the isoflurane via a system which vaporized the isoflurane and mixed it with the oxygen using an anesthesia system (EZ Anesthesia™, Euthanex).

When the mice first emerged from the anesthesia box (animals were moved from an anesthesia box to room air, including oxygen and $CO_2$), they were groggy for about 2-40 seconds. Following the brief groggy period, a supranormal function became apparent as their gait (including stride length, stance width, and swing duration) was improved relative to prior to the administration of the isoflurane.

Gait was supranormal in mice 1 minute after recovering from isoflurane anesthesia. Stride length was significantly increased [$7.6 \pm 0.2$ cm vs. $6.3 \pm 0.1$ cm, $P<0.05$] 1 minute after recovery compared to baseline values; yet stepping frequency was reduced [$3.3 \pm 0.1$ Hz vs. $4.1 \pm 0.1$ Hz, $P<0.05$]. Stance width variability was lower 1 minute after recovery from isoflurane, indicating enhanced postural stability in the mice walking on the treadmill belt. Swing duration was increased by ~50% compared to baseline 1 minute after recovery [$103 \pm 3$ ms vs. $77 \pm 3$ ms, $P<0.05$]. Additionally, propulsion duration of the hind limbs was significantly longer 1 minute after recovery than at baseline [$167 \pm 6$ ms vs. $128 \pm 5$ ms, $P<0.05$]. Some supranormal characteristics persisted for ~30 minutes, and all of the gait metrics returned to baseline within ~60 minutes following cessation of anesthesia.

It is contemplated that the supranormal gait immediately after recovery from isoflurane anesthesia may be related to the known effects of isoflurane on dopamine release in the striatum. Accordingly, isoflurane may be used for treating or preventing diseases, e.g., Parkinson's disease, where increasing dopamine release in the striatum would be desirable. The term "supranormal" is meant to convey better than nominal gait performance. Parkinson's disease and other movement disorders are usually associated with reduced stride length, or lower than average stride length. Stride length in a subject with PD could be considered significantly disturbed even when the stride length is only 10% shorter than that of an average size and age matched control subject. Therefore, when stride length is increased, e.g., robustly, the term "supranormal" is used. In the above example, some mice emerging from isoflurane anesthesia had an increased stride length of about 25%, thus the term "supranormal" is used to describe the improvement.

The specification is most thoroughly understood in light of the teachings of the references cited within the specification which are hereby incorporated by reference. The embodiments within the specification provide an illustration of embodiments in this disclosure and should not be construed to limit its scope. The skilled artisan readily recognizes that many other embodiments are encompassed by this invention. All publications and patents cited and sequences identified by accession or database reference numbers in this disclosure are incorporated by reference in their entirety. To the extent that the material incorporated by reference contradicts or is inconsistent with the present specification, the present specification will supercede any such material. The citation of any references herein is not an admission that such references are prior art to the present disclosure.

Unless otherwise indicated, all numbers expressing quantities of ingredients, cell culture, treatment conditions, and so forth used in the specification, including claims, are to be understood as being modified in all instances by the term "about." Accordingly, unless otherwise indicated to the contrary, the numerical parameters are approximations and may vary depending upon the desired properties sought to be obtained by the present invention. Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the following claims.

What is claimed is:

1. A method of treating Parkinson's disease in a subject in need thereof comprising administering a therapeutically effective amount of a halogenated volatile compound to the subject, such that the Parkinson's disease is treated or, wherein the halogenated volatile compound is selected from the group consisting of a halogenated ether, a halogenated alkane and a halogenated benzene.

2. A method of improving gait in a subject having Parkinson's disease comprising administering a therapeutically effective amount of a halogenated volatile compound to the subject and measuring stride length in the subject, wherein the halogenated volatile compound is selected from the group consisting of a halogenated ether, a halogenated alkane and a halogenated benzene, and wherein an increase in stride length in the subject following administration of the halogenated volatile compound relative to the stride length in the absence of the halogenated volatile compound is indicative of an improvement in gait.

3. A method of treating Parkinson's disease in a subject comprising: (a) administering a therapeutically effective amount of a halogenated volatile compound to the subject; and b) measuring stride length in the subject, wherein the halogenated volatile compound is selected from the group consisting of a halogenated ether, a halogenated alkane and a halogenated benzene where an increase in the stride length in the presence of the compound relative to the stride length in the absence of the compound is indicative of treatment or prevention of Parkinson's disease.

4. The method of claim 2, wherein the halogenated volatile compound is a halogenated ether.

5. The method of claim 4, wherein the halogenated ether is isoflurane.

6. The method of claim 2, wherein the halogenated volatile compound is selected from the group consisting of isoflurane, desflurane, enflurane, halothane, and sevoflurane.

7. The method of claim 6, wherein the halogenated volatile compound is in gaseous form.

8. The method of claim 7, wherein the halogenated volatile compound is administered using an inhaler.

9. The method of claim 7, wherein the halogenated volatile compound is administered using a chamber and wherein the subject is partially or wholly in the chamber.

10. The method of claim 2, wherein the stride length is measured as the subject ambulates on a treadmill.

11. The method of claim 2, wherein the subject further comprises reduced stride frequency and reduced stance width variability in the presence of the compound relative to the stride frequency and stance width variability in the absence of the compound.

12. The method of claim 6, wherein the halogenated volatile compound is administered in combination with oxygen.

13. The method of claim 6, wherein the halogenated volatile compound is administered in combination with oxygen and/or carbon dioxide.

14. The method of claim 6, wherein the halogenated volatile compound is administered to the subject with an additional therapeutic agent.

15. The method of claim 4, wherein the halogenated ether is administered in combination with oxygen.

16. The method of claim 4, wherein the halogenated ether is administered in combination with oxygen and/or carbon dioxide.

17. The method of claim 4, wherein the halogenated ether is administered to the subject with an additional therapeutic agent.

* * * * *